(12) United States Patent
Kleinert

(10) Patent No.: US 7,472,598 B2
(45) Date of Patent: Jan. 6, 2009

(54) ULTRASONIC INSPECTION APPARATUS AND METHOD FOR EVALUATING ULTRASONIC SIGNALS

(75) Inventor: Wollfgang Kleinert, Bonn (DE)

(73) Assignee: Agfa NDT GmbH, Hürth (DE)

( * ) Notice: Subject to any disclaimer, the term of this patent is extended or adjusted under 35 U.S.C. 154(b) by 448 days.

(21) Appl. No.: 10/539,853

(22) PCT Filed: Oct. 4, 2003

(86) PCT No.: PCT/DE03/03279

§ 371 (c)(1),
(2), (4) Date: Jun. 20, 2005

(87) PCT Pub. No.: WO2004/057328

PCT Pub. Date: Jul. 8, 2004

(65) Prior Publication Data

US 2006/0016263 A1   Jan. 26, 2006

(30) Foreign Application Priority Data

Dec. 19, 2002 (DE) ............................. 102 60 063
Aug. 16, 2003 (DE) ............................. 103 37 657

(51) Int. Cl.
   *G01N 29/00* (2006.01)
(52) U.S. Cl. ..................... 73/627; 73/602; 73/615; 73/628
(58) Field of Classification Search .............. 73/627, 73/599, 600, 602, 606, 616, 615, 618, 866.5, 73/865.8
   See application file for complete search history.

(56) References Cited

U.S. PATENT DOCUMENTS 4,147,065 A * 4/1979 Lather et al. ................ 73/611
4,176,658 A   12/1979 Kossoff et al.

(Continued)

FOREIGN PATENT DOCUMENTS

DE      100 58 174 A1    5/2005

OTHER PUBLICATIONS

International Search Report of PCT/DE2003/03279 dated Jun. 1, 2004.

(Continued)

*Primary Examiner*—Hezron E. Williams
*Assistant Examiner*—Jacques M. Saint-Surin
(74) *Attorney, Agent, or Firm*—McCarter & English, LLP

(57) ABSTRACT

An ultrasonic inspection apparatus for non-destructive inspection of a test body. The apparatus includes a probe, a transmitter operably connected to the probe, a receiver operably connected to the probe and a monitor with a display operably connected to the receiver for representing the echo signals received. The receiver receives echo signals. The transmitter generates transmitter pulses and delivers the transmitter pulses to the probe, wherein the probe delivers ultrasonic pulses and insonifies them at a certain angle ($\alpha$) into a test body. The pulses penetrate the test body where the test pulses are at least once reflected from a rear wall of the test body forming, as a result thereof, at least one first leg that extends from an entrance surface to the rear wall and a second leg that extends from the rear wall to the entrance surface. The echo signals received are represented on the display so as to show from which leg the echo signals originate.

23 Claims, 2 Drawing Sheets

U.S. PATENT DOCUMENTS

| | | | | |
|---|---|---|---|---|
| 4,364,274 | A | * | 12/1982 | Sharpe ........................ 73/615 |
| 4,866,986 | A | * | 9/1989 | Cichanski .................... 73/600 |
| 4,947,351 | A | * | 8/1990 | Moran et al. ................. 702/39 |
| 5,103,427 | A | * | 4/1992 | Erdol et al. ................... 367/7 |
| 5,511,425 | A | * | 4/1996 | Kleinert et al. .............. 73/627 |
| 6,138,514 | A | * | 10/2000 | Iwamoto et al. ............. 73/622 |
| 6,304,514 | B1 | * | 10/2001 | Schulze ....................... 367/98 |
| 6,327,921 | B1 | | 12/2001 | Hsu et al. |
| 7,240,554 | B2 | * | 7/2007 | Berke ........................... 73/602 |
| 2006/0109002 | A1 | * | 5/2006 | Buschke et al. ............. 324/237 |

OTHER PUBLICATIONS

V. Deutsch, M.; Platte, M. Vogt: "3.4 Fehlernachweis und Gerätejustierung" Ultraschallprüfung, 1997, pp. 80-133, XP002280036 Berlin, Heidelberg, New York.

GE Inspection Technologies: "USM 35 Ultrasonic Flaw Detector" 'Online!, XP002280037.

* cited by examiner

ULTRASONIC INSPECTION APPARATUS AND METHOD FOR EVALUATING ULTRASONIC SIGNALS

FIELD OF THE INVENTION

The invention relates to an ultrasonic inspection apparatus for non-destructive inspection of a test body. The invention further relates to a method of representing echo signals that are obtained using an ultrasonic inspection apparatus for non-destructive inspection of a test body.

DESCRIPTION OF THE RELATED ART

Suitable inspection apparatus have been known for ultrasonic non-destructive inspection of a workpiece. Generally, the reader is referred to the German book by J. and H. Krautkrämer, *Ultrasonic Testing of Materials*, sixth edition.

The angle beam probe delivers high-frequency sound pulses (about 1-10 MHz) that are sent into the workpiece to be tested and are reflected from the entrance surface back to the angle beam probe on the one side and penetrate the workpiece on the other side where they are reflected at least once from a rear wall of the workpiece. The sound waves are reflected off inner inhomogeneities such as material flaws and are again received by the angle beam probe and processed in the ultrasonic apparatus.

The method of the invention is suited for a plurality of current measurement methods; the invention will be explained hereinafter with reference to the pulse-echo method. The angle beam probe delivers ultrasonic pulses preferably periodically and later receives the echo signals of these delivered ultrasonic pulses. Generally, the echo signal from the entrance surface is a particularly strong signal that is stronger than the other echo signals. The other echo signals originate from the workpiece and more specifically from the rear wall of the workpiece. Inasmuch, the inspection method is suited for workpieces the entrance surface of which extends substantially parallel to the rear wall so that the ultrasonic pulse is reflected several times back and forth within the workpiece.

The angle beam probe is disposed next to the to-be-tested area and the sound signal is insonified into the area of concern, from the side for example. This is the case with ultrasonic inspection of weld seams, for example. The ultrasound wave enters the material until it is partially or completely reflected from an interface. If the reflecting surface is normal to the direction of propagation, the sound wave will be reflected in its initial direction and will reach, after a certain travel time, a piezoelectric crystal disposed in the angle beam probe that converts the sound wave back into an electrical pulse. The return ultrasound is again reflected from the interface crystal-workpiece surface with this small sound portion travelling a second time through the workpiece. Thus, what is termed an echo sequence is produced by multiple reflection from interfaces (rear wall of the part being tested or flaw) when using the pulse-echo method.

Accordingly, when the test body has no flaws, the sound is reflected between the entrance surface and the rear wall of the test body and continues to penetrate the test body at a certain angle in the direction away from the angle beam probe.

When inspecting weld seams, the angle beam probe is caused to move along the weld seam until a maximal flaw echo signal is produced. The echo signals received are directly displayed on the monitor. Generally, they are displayed as what is termed an A-scan in which the voltage values of the echo signals received are plotted down the side of the scan or along the vertical axis whereas time is plotted on the horizontal axis. As the sound wave is reflected back and forth several times between the entrance surface and the rear wall, a sequence of uniformly spaced echo signals are produced, the amplitude of which generally decreases with increasing time. The discrete back and forth movements, meaning the distance the sound travels from the entrance surface to the rear wall and back is referred to as a leg. Starting from the angle beam probe, a first leg, which extends at an incline from the entrance surface toward the rear wall, is first produced. From there, the sound is reflected, forming a second leg that extends from the rear wall toward the entrance surface, and so on.

Because of the inclined orientation of the sound paths, the location of a reflector (flaw) in the test piece may only be determined by geometrical considerations and is computed on the basis of the known and measured data.

For a successful manual inspection of the test body, it is necessary that the inspector scans the test bodies with constant accuracy using the angle beam probe. This is the only known way to achieve a result that is sufficiently precise. Also, this is necessary for documenting the test later. When testing large test bodies in particular, and more specifically, when testing long weld seams, it may happen that the inspector, lacking concentration, inaccurately follows the distance to be scanned.

Using the prior art measurement methods, the inspector must therefore keep an eye on the test body at all times and does not receive any feedback from the monitor about the position of the angle beam probe with respect to the weld seam to be tested, for example. As a result, the inspector must always alternately have a look on the monitor and on the test body. If, for instance, he detects a flaw on the monitor, that is to say, in the A-scan, and if he reacts too late, the inspector's hand holding the angle beam probe has already moved away from the critical site. As the inspector only looked on the monitor, it will be quite difficult for him to find the position of concern.

SUMMARY OF THE INVENTION

The present disclosure is directed to facilitating the work of the inspector. The present disclosure aims at developing a method of evaluating ultrasonic signals produced using an angle beam probe by which the inspector is already provided with additional information during testing so that it is easier for the inspector to inspect the test body. The present disclosure is more specifically intended to provide the inspector with auxiliary information that will make it easier for him to precisely guide the angle beam probe as required.

In accordance with the present disclosure, this is achieved both by an ultrasonic inspection apparatus and by a method by which the received electric echo signals are represented on the display so as to show from which leg they originate.

This means that the inspector can recognize at first glance whether a detected relevant signal such as a defect displayed on the monitor is located in the region of the first, the second or another leg. The distance between the relevant signal and the angle beam probe can be directly inferred therefrom. This makes it much easier for the inspector to inspect the test body since a look on the monitor will provide the inspector with readily understandable information about the position of the angle beam probe. If, during testing, the inspector sees a relevant signal displayed on the monitor, the inspector will immediately know the distance between the origin of the signal, the defect for example, and the angle beam probe. This tremendously facilitates the work of the inspector.

The present disclosure is not only suited for manual testing of test bodies, it also is of assistance in the automatic scanning of a test body by means of an angle beam probe. The reason therefore is that, at a glance on the monitor, an inspector who does not manually control the travel of the angle beam probe immediately infers from the representation whether the site to be tested, such as the weld seam, is located in the right leg of the sound path and whether, as a result thereof, the angle beam probe is spaced the correct distance apart from the weld seam.

As used herein, the term flaw is not only meant literally, that is, to refer to discontinuities, but is also to be construed as a significant signal. Accordingly, the invention also includes finding any relevant location in a test body.

The prerequisite for such a system is the known insonification angle and the known wall thickness of the test body. The sound path for one leg and, as a result thereof, the transition from one leg to the next or the point at which the sound is reflected from the entrance surface or from the rear wall can be readily calculated from this information.

The different representation on the monitor of the legs or of the regions corresponding to a respective one of the legs can be performed using any suited representation method.

The portion of the measured curve that is associated with a certain leg can, for example, be marked by a particular hatching or by a particular shade of grey of the background. This means that the measured curve itself remains unchanged. The information on which leg the respective portion of the measured curve is based is generated by the background.

Alternatively, an additional symbol may be envisaged at those points on the measured curve at which the sound is reflected from the entrance surface or from the rear wall. These points correspond to the transitions from one leg to the next. Such symbols can be alphanumeric characters or dashed lines that intersect the measured curve for example.

In a particularly advantageous implementation variant, the monitor comprises a color display. Depending on the leg on which the measured curve is based, said measured curve may then be represented in different colors. The use of strong colors such as primary colors is advisable here. Also, the background of the measured curve can be represented accordingly in different colors. Beside LCD displays, other color monitors such as plasma displays have proved efficient.

In another advantageous implementation variant, the angle beam probe comprises a calliper for recording the zero point position at the beginning of the inspection procedure. This means that inspection starts at a defined location on the test body, the location being stored in the system. This permits relevant positions of the angle beam probe to be later reconstructed on the basis of the stored data. For this purpose, the angle beam probe comprises means that serve to indicate the respective position on the surface of the body to be tested with respect to the location at the beginning of measurement. This can be performed using, for example, a digital camera that is solidly connected to the housing of the angle beam probe. The digital camera is oriented so as to capture the surface of the body to be tested. It is anticipated that the digital camera delivers an image of the surface of the body in proximity to the very location at which a central beam of the active sound element passes through the surface. At intervals, an electronic image of the surface portion which is respectively located beneath the lens of the digital camera, which accordingly lies in the object plane, is captured by means of this digital camera. The portion may have dimensions of a few millimeters, for example, such as 2×2 or 4×4 mm. Preferably, at given fixed intervals, the digital camera captures an image of the respective surface portion. The reader is referred in this context to the application DE 100 58 174 A1 of the applicant.

Also it can be advantageous if only that region of the test body to be inspected is represented on the monitor or on the display that is of interest for testing. This may, for example, be the weld seam to be tested. If the weld seam geometry is known and stored in the ultrasonic inspection apparatus or in the computer, both spatial limits and limits with respect to the amplitude to be taken into consideration may be entered. If, at the beginning of the measurement, the zero point position has been located, the distance of the angle beam probe from the weld seam can be computed any time based on the leg length or the wall thickness and on the insonification angle. Accordingly, it is possible to represent on the monitor, any time and independent of the position of the angle beam probe, the mere region of the weld seam. In this very case, it is particularly advantageous to represent the legs differently. The reason therefore is that, if the correct distance from the weld seam is maintained, a possible flaw or a relevant signal always has to occur in the same leg and the monitor and/or the measured curve accordingly always has to show the same representation.

Depending on the movement of the angle beam probe, it is of course possible that the relevant signal has to occur in a path length of two or three legs for example, so that the representation varies accordingly.

At a glance on the monitor and without an additional glance on the test body, a change in the representation will immediately tell the inspector whether he has moved the angle beam probe too far away from the weld seam.

It may for instance also be advantageous not to have the various legs represented in a particular way but to rather have a back and forth movement, that is to say two legs joined together, represented in the same way. Also, portions of several legs can be represented in the same way accordingly. It is also possible to represent differently the various back and forth movements between the entrance surface and the rear wall when inspecting a test body with an ultrasonic inspection apparatus that is insonifying the test body. Finally, it may be sensible not to have the representation of the measured curve be dependent on the origin of the measured data but to only have it determined by time windows fixed in advance. For example, after a certain time interval, the measured curve can be represented in yellow to then be shown in another color after a certain time.

BRIEF DESCRIPTION OF THE DRAWINGS

Other features and advantages will become more apparent upon reviewing the appended claims and the following non restrictive description of embodiments of the invention, given by way of example only with reference to the drawing. In said drawing:

DETAILED DESCRIPTION

Figure 1:
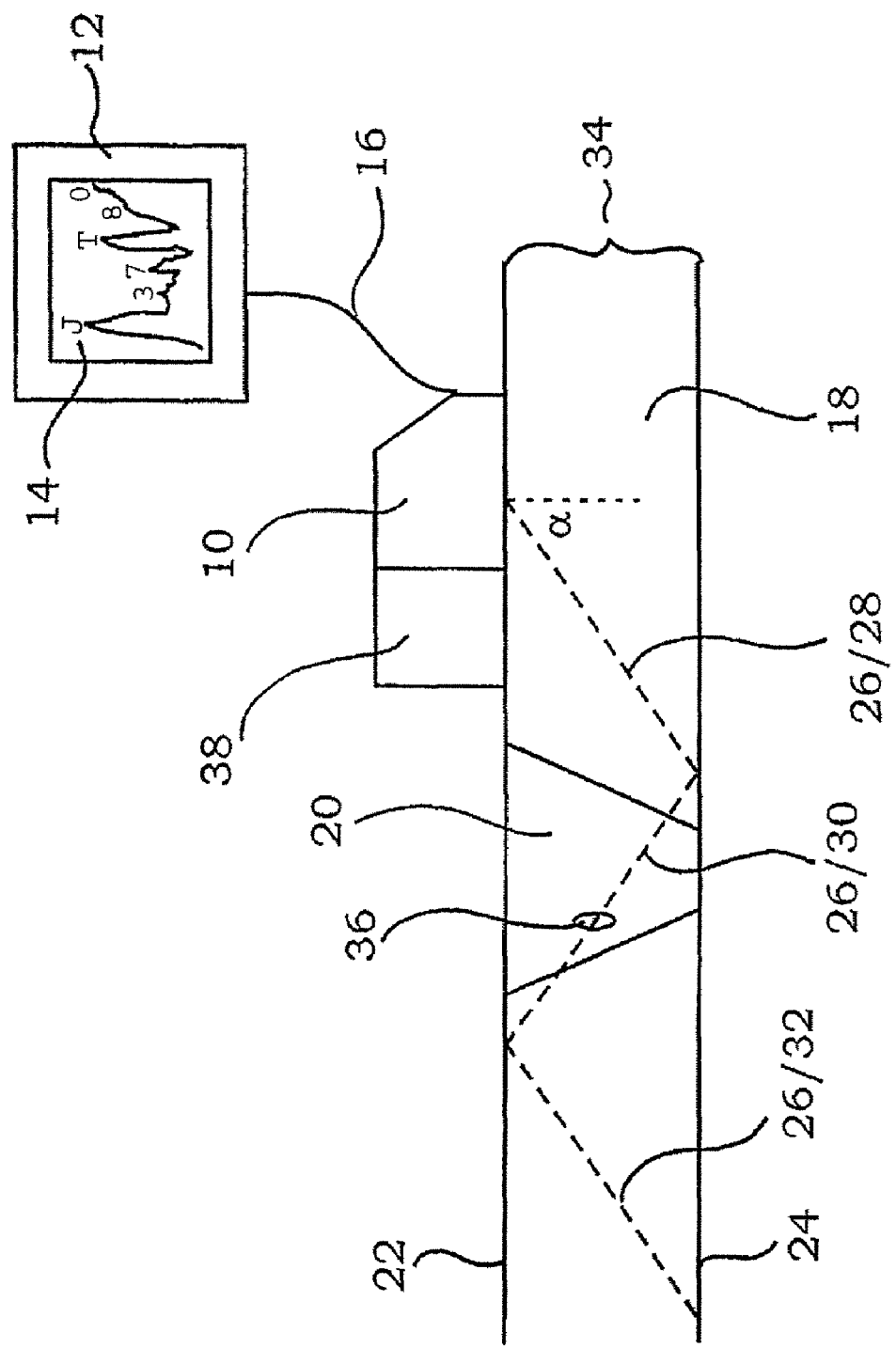
FIG. 1: is a schematic diagram of the sound path of an ultrasonic signal taking departure from an angle beam probe and passing through a test body.

FIG. 1 is a cross-sectional view of the basic structure of an ultrasound measurement using an angle beam probe 10 as the ultrasonic measurement apparatus. The angle beam probe 10, which includes a transmitter and a receiver, is connected by a wire cable 16 to a monitor 12, which in turn comprises a display 14. It may also be envisaged to use another kind of connection such as a wireless connection instead of the wire cable 16.

The angle beam probe 10 is disposed on a test body 18. The test body 18 here is a portion of a steel plate that is connected through a weld seam 20 to a second steel plate. The test body 18 comprises an entrance surface 22 and a rear wall 24. Between the entrance surface 22 and the rear wall 24, a sound path 26 is shown by a line. Taking departure from the angle beam probe 20, transmitter pulses, that is to say the sound, is first insonified obliquely into the test body 18 at a predetermined angle α, forms a first leg 28, is then reflected from the rear wall 24, forms a second leg 30, returns back to the entrance surface 22, is reflected again and forms a third leg 32 and so on. In the exemplary representation, the sound path 26 intersects the weld seam 20 in the region of its second leg 30. It is readily possible to compute, from a wall thickness 34 and the angle α, the length of a leg 28, 30, 32 or the point of transition from one leg 28, 30, 32 to the next.

If the sound hits a flaw 36 such as an air bubble, it is reflected as an echo signal back to the receiver depending on the orientation of the flaw. Now knowing which leg 28, 30, 32 has hit the flaw 36, the inspector can now directly infer the approximate distance between the flaw 36 and the angle beam probe 10; the inspector then at least knows that the flaw is located on the path portion of the corresponding leg 28, 30, 32.

In another advantageous implementation variant, the angle beam probe 10 comprises a calliper for recording the zero point position at the beginning of the inspection procedure. This means that inspection starts at a defined place on the test body, this place being stored in the system. For this purpose, the angle beam probe 10 comprises a means 38 that is solidly connected to the angle beam probe 10 and serves to indicate the respective position on the surface of the body to be tested with respect to the position at the beginning of measurement. This may be achieved using a digital camera that is solidly connected to the housing of the angle beam probe. It is oriented so as to capture the surface of the test body.

Figure 2:
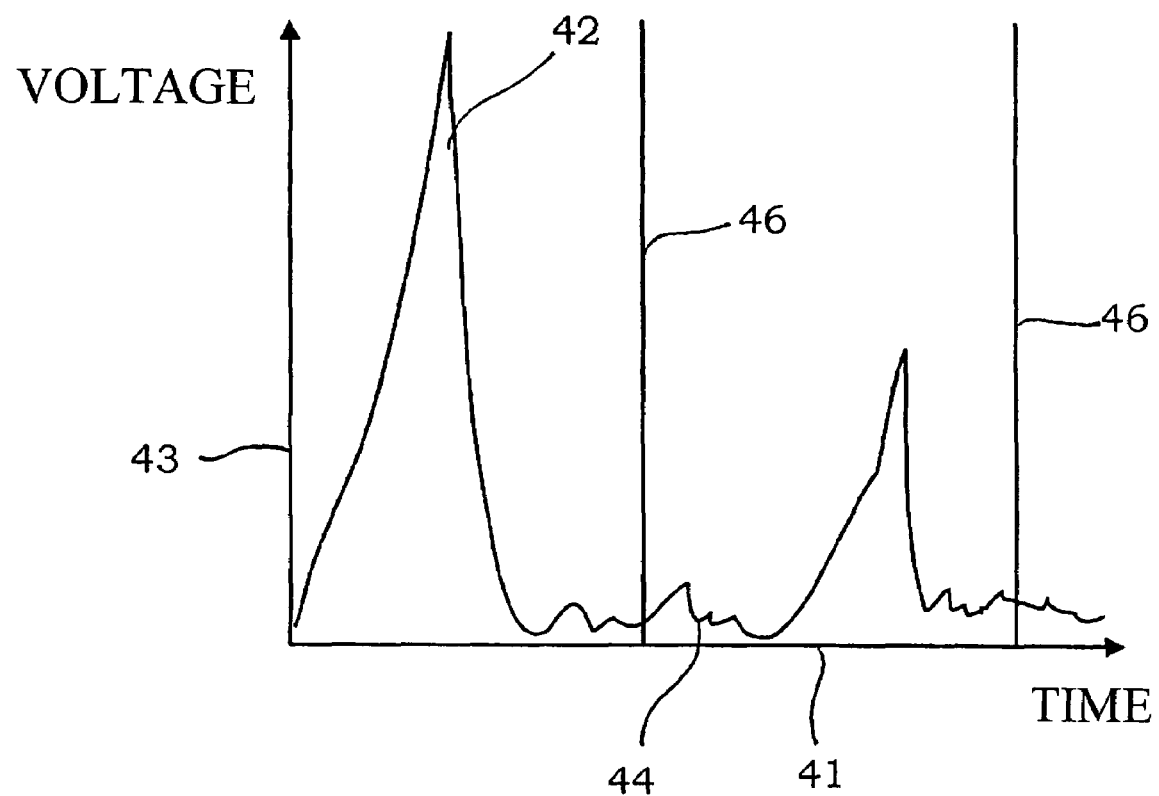
FIG. 2 shows an exemplary representation, in accordance with the invention, of an A-scan.

FIG. 2 is a schematic diagram showing what is termed an A-scan 40 that is represented on the display 14 of the monitor 12. The voltage values U in V of the echo signals received are plotted down the side of the scan on the y-axis (the voltage value axis 43) whereas time is plotted in seconds on a horizontal time axis 41 (the x-axis).

The transmitter periodically delivers transmitter pulses that cause the angle beam probe 10 to deliver short ultrasonic pulses. The various ultrasonic pulses first travel through a coupling means. A part of each pulse is generally reflected from the entrance surface 22 and arrives as an entrance echo 42 in time before other signals in the receiver. Generally, one part of each ultrasonic pulse penetrates the workpiece and is, as already explained, reflected from the rear wall 24 and accordingly propagates in the test body between the entrance surface 22 and the rear wall 24. The illustrated measured curve 44 is obtained. Moreover, a part of the ultrasonic pulse that has penetrated the workpiece is also reflected from defects such as the flaw 36, provided such defects exist.

The ultrasonic measuring apparatus, or a computer cooperating therewith, computes the positions at which the one leg 28, 30, 32 merges into the next one, that is to say, at which the sound is reflected from the entrance surface 22 or from the rear wall 24. In accordance with the invention, these data are employed to visually represent the various legs 28, 30, 32 on the display 14. As shown in FIG. 2, this may be shown by lines 46 that intersect the measured curve 44 at the corresponding places. Alternatively, the background of the measured curve 44 could also be devised according to the legs 28, 30, 32 and could, for example, be hatched or colored with different shades of grey.

The use of a color display has proved very advantageous because it allows both to simplify and to make more visible the marking of the portions of the measured curve 44 corresponding to the discrete legs 28, 30, 32. The backgrounds of the measured curve 44 may then be highlighted in different colors or the measured curve 44 itself can comprise different colors depending on the origin of the data originating from the respective one of the legs 28, 30, 32.

It may also be advantageous that only that region of the test body 18 to be inspected is represented on the monitor 12 or on the display 14 that is of interest for testing. This may for example be the weld seam 20 to be tested. Both spatial limits and limits relative to the amplitudes to be taken into consideration are entered and regarded. This means that only those signals are displayed that originate from either the region of the to-be-tested weld seam 20 and/or the intensity of which exceeds the minimal limit and/or remains below the maximal limit. This also facilitates the work of the inspector.

From what has been said herein above, it is obvious that the apparatus of the present disclosure, and in particular, the method of inspecting workpieces performed therewith, are suited for serial measurement. An example of a serial measurement is the inspection of weld connections of automobile bodyworks. The inspection apparatus is first adjusted on a workpiece or on a few workpieces prior to performing serial testing.

The present disclosure is not limited to the exemplary embodiments described but also covers all the other equivalents.

The invention claimed is:

1. An ultrasonic inspection apparatus for non-destructive inspection of a test body, the apparatus comprising:
   a probe;
   a transmitter operably connected to the probe, the transmitter generates transmitter pulses and delivers the transmitter pulses to the probe;
   a receiver operably connected to the probe, the receiver receives echo signals; and
   a monitor with a display operably connected to the receiver for representing the echo signals received, in the form of an A-scan,
   wherein the probe delivers ultrasonic pulses and insonifies them at a certain angle (α) into a test body, the pulses penetrating the test body where the test pulses are at least once reflected from a rear wall of the test body forming, as a result thereof, at least one first leg that extends from an entrance surface to the rear wall and a second leg that extends from the rear wall to the entrance surface,
   wherein the echo signals received are represented on the display within the A-scan so as to show from which leg the echo signals originate.

2. The ultrasonic inspection apparatus as set forth in claim 1, wherein the echo signals on the display are represented in a diagram in the form of a measured curve, with time being plotted on a horizontal axis and voltage values on a vertical axis.

3. The ultrasonic inspection apparatus as set forth in claim 2, wherein an alphanumeric character is associated with respective points of the measured curve that correspond to a respective transition from one leg to a next leg.

4. The ultrasonic inspection apparatus as set forth in claim 2, wherein a line intersects the measured curve at a respective one of respective points of the measured curve that correspond to a transition from one leg to a next leg.

5. The ultrasonic inspection apparatus as set forth in claim 2, wherein portions of the measured curve that originate from a certain leg are shown on a background that is typical for a respective one of the legs.

6. The ultrasonic inspection apparatus as set forth in claim 2, wherein the display is a color display.

7. The ultrasonic inspection apparatus as set forth in claim 6, wherein portions of the measured curve that originate from a certain leg are placed on a colored background that is typical for a respective one of the legs.

8. The ultrasonic inspection apparatus as set forth in claim 6, wherein in the regions that originate from a certain leg, the measured curve is shown by a color that is typical for a respective one of the legs.

9. The ultrasonic inspection apparatus as set forth in claim 2, wherein in the regions that originate from a certain leg, the measured curve is shown by a kind of line that is typical for a respective one of the legs.

10. The ultrasonic inspection apparatus as set forth in claim 1, wherein the display is a color display.

11. The ultrasonic inspection apparatus as set forth in claim 1, further comprising:
a means for determining a respective position of the probe on the surface of the test body, the means being operably connected to the probe.

12. The ultrasonic inspection apparatus as set forth in claim 1, wherein only a region of the test body to be tested is represented on the display that is of interest for inspection, taking into consideration limit values in terms of at least one of amplitude and spatial limits.

13. A method of representing echo signals obtained using an ultrasonic inspection apparatus for non-destructive inspection of a test body, the ultrasonic inspection apparatus comprising:
a probe,
a transmitter operably connected to the probe, the transmitter generating transmitter pulses and delivering the transmitter pulses to the probe,
a receiver operably connected to the probe, the receiver receiving echo signals; and
a monitor with a display operably connected to the receiver for representing the echo signals received in the form of an A-scan, the method comprising the following method steps:
delivering ultrasonic pulses through the probe;
insonifying the ultrasonic pulses into the test body at a certain angle ($\alpha$) such that the ultrasonic pulses penetrate the test body where the ultrasonic pulses are reflected at least once from a rear wall of the test body and form, as a result thereof, a first leg that extends from an entrance surface to the rear wall and a second leg that then extends from the rear wall to the entrance surface; and
representing the echo signals received on the display within the A-scan, wherein the echo signals received are represented on the display so as to show from which leg the echo signals originate.

14. The method as set forth in claim 13, wherein the echo signals on the display are represented in a diagram in a form of a measured curve, with time being plotted on a horizontal axis and a voltage value on a vertical axis.

15. The method as set forth in claim 14, wherein an alphanumeric character is associated with respective points of the measured curve that correspond to a respective transition from one leg to a next leg.

16. The method as set forth in claim 14, wherein a line intersects the measured curve at a respective one of respective points of the measured curve that correspond to a transition from one leg to a next leg.

17. The method as set forth in claim 14, wherein portions of the measured curve that originate from a certain leg are placed on a background that is typical for a respective one of the legs.

18. The method as set forth in claim 14, wherein regions that originate from a certain leg, the measured curve is shown by a kind of line that is typical for a respective one of the legs.

19. The method as set forth in claim 13, wherein the display is a color display

20. The method as set forth in claim 19, wherein portions of the measured curve that originate from a certain leg are placed on a colored background that is typical for a respective one of the legs.

21. The method as set forth in claim 19, wherein regions that originate from a certain leg, the measured curve is shown by a color that is typical for a respective one of the legs.

22. The method as set forth in claim 13, further comprising:
a means for determining a respective position of the probe on the surface of the test body, the means being operably connected to the probe.

23. The method as set forth in claim 13, wherein only a region of the test body to be tested is represented on the display that is of interest for inspection, taking into consideration limit values in terms of at least one of amplitude and spatial limits.

* * * * *

UNITED STATES PATENT AND TRADEMARK OFFICE
CERTIFICATE OF CORRECTION

PATENT NO. : 7,472,598 B2 Page 1 of 1
APPLICATION NO. : 10/539853
DATED : January 6, 2009
INVENTOR(S) : Wolfgang Kleinert It is certified that error appears in the above-identified patent and that said Letters Patent is hereby corrected as shown below:

On the Title page, item [75] Inventor, delete "Wollfgang" and insert --Wolfgang--

Signed and Sealed this

Seventeenth Day of March, 2009

JOHN DOLL
*Acting Director of the United States Patent and Trademark Office*